United States Patent [19]
Herrmann et al.

[11] Patent Number: 5,670,436
[45] Date of Patent: Sep. 23, 1997

[54] METALLOCENE COMPOUND

[75] Inventors: Hans-Friedrich Herrmann, Dornheim; Michael Aulbach, Hofheim; Frank Küber, Oberursel, all of Germany

[73] Assignee: Hoechst AG, Germany

[21] Appl. No.: 540,201

[22] Filed: Oct. 6, 1995

[30] Foreign Application Priority Data

Oct. 10, 1994 [DE] Germany .................. 44 36 113.0

[51] Int. Cl.$^6$ .............. C07F 17/00; C07F 7/00; C08F 4/64; C08F 4/642
[52] U.S. Cl. .............. 502/103; 502/117; 526/127; 526/160; 526/348.2; 526/348.5; 526/943; 556/11; 556/12; 556/28; 556/23; 556/43; 556/53; 556/58
[58] Field of Search .............. 556/11, 12, 22, 556/23, 43, 53, 58; 502/103, 117; 526/160, 943, 127, 348.2, 348.5

[56] References Cited

U.S. PATENT DOCUMENTS

| | | | |
|---|---|---|---|
| 5,296,434 | 3/1994 | Karl et al. | 502/117 |
| 5,455,366 | 10/1995 | Rohrmann et al. | 556/8 |
| 5,468,440 | 11/1995 | McAlpin et al. | 264/291 |
| 5,514,760 | 5/1996 | Karl et al. | 526/127 |
| 5,532,396 | 7/1996 | Winter et al. | 556/11 |
| 5,543,373 | 8/1996 | Winter et al. | 502/103 |
| 5,545,829 | 8/1996 | Brekner et al. | 526/160 |
| 5,556,997 | 9/1996 | Strickler et al. | 556/11 |
| 5,565,534 | 10/1996 | Aulbach et al. | 526/160 |
| 5,576,260 | 11/1996 | Winter et al. | 502/117 |
| 5,578,537 | 11/1996 | Herrmann et al. | 502/120 |
| 5,585,508 | 12/1996 | Kuber et al. | 556/11 |

*Primary Examiner*—Porfirio Nazario-Gonzalez
*Attorney, Agent, or Firm*—Connolly and Hutz

[57] ABSTRACT

The present invention relates to an unbridged metallocene compound which is suitable for olefin polymerization.

19 Claims, No Drawings

METALLOCENE COMPOUND

The present invention relates to a metallocene compound which is suitable as catalyst component for olefin polymerization. The invention also relates to a process for preparing polyolefins using the metallocene compound of the invention.

Bridged metallocenes are known (EP 284 708, EP 344 887). In their synthesis, there is formed not only the desired racemic compound but equally also the meso compound which, in the polymerization of 1-olefins, is not suitable for the preparation of isotactic polymers and which generally shows a significantly lower polymerization activity. The preparation of high-performance polyolefin materials therefore requires the complicated removal of the meso form.

Furthermore, processes are known for preparing polyethylene and ethylene/1-olefin copolymers using stereorigid metallocenes containing bridged, substituted cyclopentadienyl ligands (EP 399348). This concept was developed further in WO 9324536 using doubly bridged metallocenes for preparing (co)polymers.

Furthermore, unbridged metallocenes are known for preparing polyolefins (EP 69951, EP 129368, EP 170059, EP 206794, EP 285443 or EP 294942). These unbridged metallocenes are, in particular, cyclopentadienylzirconium complexes whose cyclopentadienyl radicals are substituted or unsubstituted. Disadvantages of these unbridged metallocenes are the low degree of comonomer incorporation and the fact that high comonomer concentrations are required in the preparation of low-density copolymers.

It is therefore an object of the invention to provide a metallocene compound which avoids the disadvantages of the prior art.

It has now been found that this object is achieved by a specific unbridged metallocene compound.

The present invention accordingly provides a metallocene compound of the formula (I)

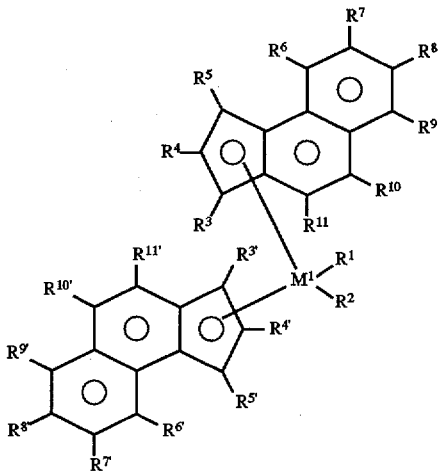

where $M^1$ is a metal of group IVb, Vb or VIb of the Periodic Table, $R^1$ and $R^2$ are identical or different and are each a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_8$–$C_{40}$-arylalkenyl group, an OH group or a halogen atom, the radicals $R^3$, $R^4$, $R^5$, $R^6$, $R^7$, $R^8$, $R^9$, $R^{10}$ and $R^{11}$ are identical or different and are each a hydrogen atom, a halogen atom, a $C_1$–$C_{20}$-hydrocarbon radical which may be halogenated, an —$NR_2$, —$SR$, —$OR$, —$OSiR_3$, —$SiR_3$ or $PR_2$ radical, where R is a halogen atom, a $C_1$–$C_{10}$-alkyl group or a $C_6$–$C_{10}$-aryl group, or two or more of the radicals $R^3$, $R^4$, $R^5$, $R^6$, $R^7$, $R^8$, $R^9$, $R^{10}$ and $R^{11}$ together with the atoms connecting them form a ring system, and the radicals $R^{3'}$, $R^{4'}$, $R^{5'}$, $R^{6'}$, $R^{7'}$, $R^{8'}$, $R^{9'}$, $R^{10'}$ and $R^{11'}$ are identical or different and are each a hydrogen atom, a halogen atom, a $C_1$–$C_{20}$-hydrocarbon radical which may be halogenated, an —$NR_2$, —$SR$, —$OR$, —$OSiR_3$, —$SiR_3$ or $PR_2$ radical, where R is a halogen atom, a $C_1$–$C_{10}$-alkyl group or a $C_6$–$C_{10}$-aryl group, or two or more of the radicals $R^{3'}$, $R^{4'}$, $R^{5'}$, $R^{6'}$, $R^{7'}$, $R^{8'}$, $R^{9'}$, $R^{10'}$ and $R^{11'}$ together with the atoms connecting them form a ring system.

$M^1$ is preferably a metal of group IVb such as titanium, zirconium or hafnium. $R^1$ and $R^2$ are preferably identical or different, preferably identical, and are each a $C_1$–$C_{10}$-alkyl group, a $C_7$–$C_{15}$-arylalkyl group or a halogen atom such as fluorine, chlorine, bromine or iodine, in particular chlorine. The radicals $R^3$, $R^4$, $R^5$, $R^6$, $R^7$, $R^8$, $R^9$, $R^{10}$ and $R^{11}$ are identical or different and are preferably each a hydrogen atom, a $C_1$–$C_{20}$-hydrocarbon radical such as a $C_1$–$C_{20}$-alkyl group, a $C_6$–$C_{14}$-aryl group, a $C_2$–$C_{20}$-alkenyl group, a $C_7$–$C_{40}$-arylalkyl group or a $C_8$–$C_{40}$-arylalkenyl group, or two or more of the radicals $R^3$, $R^4$, $R^5$, $R^6$, $R^7$, $R^8$, $R^9$, $R^{10}$ and $R^{11}$ together with the atoms connecting them form a ring system. The radicals $R^{3'}$, $R^{4'}$, $R^{5'}$, $R^{6'}$, $R^{7'}$, $R^{8'}$, $R^{9'}$, $R^{10'}$ and $R^{11'}$ are preferably identical or different and are each a hydrogen atom, a $C_1$–$C_{20}$-hydrocarbon radical such as a $C_1$–$C_{20}$-alkyl group, a $C_6$–$C_{14}$-aryl group, a $C_2$–$C_{20}$-alkenyl group, a $C_7$–$C_{40}$-arylalkyl group or a $C_8$–$C_{40}$-arylalkenyl group, or two or more of the radicals $R^{3'}$, $R^{4'}$, $R^{5'}$, $R^{6'}$, $R^{7'}$, $R^{8'}$, $R^{9'}$, $R^{10'}$ and $R^{11'}$ together with the atoms connecting them form a ring system.

Particular preference is given to compounds of the formula I in which $M^1$ is a metal of group IVb, in particular zirconium.

$R^1$ and $R^2$ are identical or different, in particular identical, and are particularly preferably each a $C_1$–$C_{10}$-alkyl group such as methyl, ethyl, propyl, butyl or heptyl or a halogen atom such as chlorine.

$R^3$ and $R^5$ are identical or different and are particularly preferably each a hydrogen atom, methyl, ethyl, propyl, phenyl, benzyl, tolyl, vinyl or trimethylsilyl, in particular a hydrogen atom. $R^4$ is particularly preferably a hydrogen atom or a $C_1$–$C_{10}$-alkyl group such as methyl, ethyl, propyl, butyl or heptyl. $R^6$, $R^7$, $R^8$ and $R^{10}$ are identical or different and are particularly preferably each a hydrogen atom, a $C_1$–$C_{10}$-alkyl group such as methyl, ethyl, propyl, butyl or heptyl or a $C_6$–$C_{10}$-aryl group such as phenyl or naphthyl. $R^9$ and $R^{10}$ are identical or different and are particularly preferably each a hydrogen atom or a $C_1$–$C_{10}$-alkyl group such as methyl, ethyl, propyl, butyl or heptyl, or $R^9$ and $R^{10}$ together with the atoms connecting them form a ring system. $R^{3'}$ and $R^{5'}$ are identical or different and are particularly preferably each a hydrogen atom, methyl, ethyl, propyl, phenyl, benzyl, tolyl, vinyl or trimethylsilyl, in particular a hydrogen atom. $R^{4'}$ is particularly preferably a hydrogen atom or a $C_1$–$C_{10}$-alkyl group such as methyl, ethyl, propyl, butyl or heptyl. $R^{6'}$, $R^{7'}$, $R^{8'}$ and $R^{11'}$ are identical or different and are particularly preferably each a hydrogen atom, a $C_1$–$C_{10}$-alkyl group such as methyl, ethyl, propyl, butyl or heptyl or a $C_6$–$C_{10}$-aryl group such as phenyl or naphthyl. $R^{9'}$ and $R^{10'}$ are identical or different and are particularly preferably each a hydrogen atom or a $C_1$–$C_{10}$-alkyl group such as methyl, ethyl, propyl, butyl or heptyl, or $R^{9'}$ and $R^{10'}$ together with the atoms connecting them form a ring system.

Examples which may be mentioned of metallocene compounds of the invention having the formula I are:
bis(2-methyl-4,5-benzoindenyl)zirconium dichloride,
bis(4,5-benzoindenyl)zirconium dichloride,
bis(2-methyl-α-acenaphthylindenyl)zirconium dichloride,
bis(2-ethyl-α-acenaphthylindenyl)zirconium dichloride,
bis(α-acenaphthylindenyl)zirconium dichloride,
(2-methyl-4,5-benzoindenyl)(4,5-benzoindenyl)zirconium dichloride,
(2-methyl-4,5-benzoindenyl)(2-methyl-α-acenaphthylindenyl)zirconium dichloride,
bis(2-methyl-4,5-benzoindenyl)titanium dichloride,
bis(2-methyl-4,5-benzoindenyl)hafnium dichloride,
bis(2-methyl-4,5-benzoindenyl)dimethylzirconium,
bis(4,5-benzoindenyl)dimethylzirconium.

The metallocene compounds of the invention can be prepared by deprotonating an indene, for example, of the formula Ia,

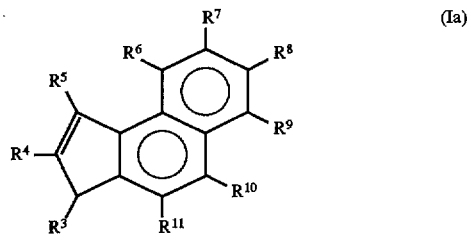

(e.g. using butyllithium) and reacting it with a metal halide such as $ZrCl_4$.

The present invention also provides a process for preparing an olefin polymer by polymerization of at least one olefin in the presence of a catalyst comprising at least one metallocene compound and a cocatalyst, wherein the metallocene is a compound of the formula I. The term polymerization includes both homopolymerization and copolymerization.

Preference is given to homopolymerizing or copolymerizing olefins of the formula $R^a$—CH=CH—$R^b$, where $R^a$ and $R^b$ are identical or different and are each a hydrogen atom or a hydrocarbon radical having from 1 to 20 carbon atoms, in particular from 1 to 10 carbon atoms, or $R^a$ and $R^b$ together with the atoms connecting them form one or more rings. Examples of such olefins are 1-olefins such as ethylene, propylene, 1-butene, 1-pentene, 1-hexene, 4-methyl-1-pentene or 1-octene, styrene, dienes such as 1,3-butadiene or 1,4-hexadiene and cyclic olefins such as norbornene, tetracyclododecene, norbornadiene or vinylnorbornene. In the process of the invention, preference is given to homopolymerizing ethylene or copolymerizing ethylene with one or more 1-olefins having from 3 to 20 carbon atoms, such as propylene, and/or one or more dienes having from 4 to 20 carbon atoms, such as 1,4-butadiene. Examples of such copolymers are ethylene/propylene copolymers and ethylene/propylene/1,4-hexadiene copolymers.

The polymerization is preferably carried out at a temperature of from −60° to 250° C., particularly preferably from 50° to 200° C. The pressure is preferably from 0.5 to 2000 bar, particularly preferably from 5 to 64 bar.

The polymerization can be carried out in solution, in bulk, in suspension or in the gas phase, continuously or batchwise, in one or more stages. A preferred embodiment is gas-phase polymerization.

The catalyst used in the process of the invention preferably contains one metallocene compound of the formula I. It is also possible to use mixtures of two or more metallocene compounds of the formula I, or mixtures of metallocene compounds of the formula I with bridged metallocenes, e.g. for preparing polyolefins having a broad or multimodal molecular weight distribution.

Suitable cocatalysts in the process of the invention are in principle all compounds which, owing to their Lewis acidity, can convert the neutral metallocene into a cation and stabilize the latter ("labile coordination"). In addition, the cocatalyst or the anion formed from it should undergo no further reactions with the metallocene cation formed (EP 427 697). The cocatalyst used is preferably an aluminum compound and/or a boron compound.

The boron compound preferably has the formula $R^{12}_xNH_{4-x}BR^{13}_4$, $R^{12}_xPH_{4-x}BR^{13}_4$, $R^{12}_3CBR^{13}_4$ or $BR^{13}_3$, where x is a number from 1 to 4, preferably 3, the radicals $R^{12}$ are identical or different, preferably identical, and are $C_1$–$C_{10}$-alkyl or $C_6$–$C_{18}$-aryl, or two radicals $R^{12}$ together with the atoms connecting them form a ring, and the radicals $R^{13}$ are identical or different, preferably identical, and are $C_6$–$C_{18}$-aryl which can be substituted by alkyl, haloalkyl or fluorine. In particular, $R^{12}$ is ethyl, propyl, butyl or phenyl and $R^{13}$ is phenyl, pentafluorophenyl, 3,5-bistrifluoromethylphenyl, mesityl, xylyl or tolyl (EP 277 003, EP 277 004 and EP 426 638).

The cocatalyst used is preferably an aluminum compound such as aluminoxane and/or an aluminum alkyl.

The cocatalyst used is particularly preferably an aluminoxane, in particular of the formula IIa for the linear type and/or the formula IIb for the cyclic type,

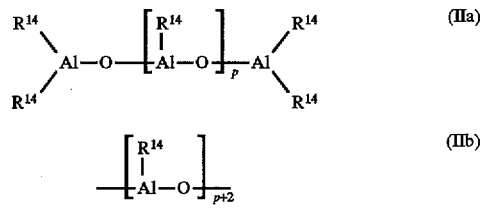

where, in the formulae IIa and IIb, the radicals $R^{14}$ are identical or different and are each hydrogen or a $C_1$–$C_{20}$-hydrocarbon group such as a $C_1$–$C_{18}$-alkyl group, a $C_6$–$C_{18}$-aryl group or benzyl, and p is an integer from 2 to 50, preferably from 10 to 35.

The radicals $R^{14}$ are preferably identical and are hydrogen, methyl, isobutyl, phenyl or benzyl, particularly preferably methyl.

If the radicals $R^{14}$ are different, they are preferably methyl and hydrogen or alternatively methyl and isobutyl, where hydrogen or isobutyl are preferably present in a numerical proportion of from 0.01 to 40% (of the radicals $R^{14}$).

The processes for preparing the aluminoxanes are known (DE 4 004 477).

The exact spatial structure of the aluminoxanes is not known (J. Am. Chem. Soc. (1993) 115, 4971). For example, it is conceivable that chains and rings join to form larger two-dimensional or three-dimensional structures.

Regardless of the method of preparation, all aluminoxane solutions have in common a variable content of unreacted aluminum starting compound which is present in free form or as adduct.

It is possible to preactivate the metallocene compound of the invention with a cocatalyst, in particular an aluminoxane, prior to use in the polymerization reaction. This significantly increases the polymerization activity. The preactivation of the metallocene compound is preferably carried out in solution. The metallocene compound is here preferably dissolved in a solution of the aluminoxane in an inert hydrocarbon. Suitable inert hydrocarbons are aliphatic or aromatic hydrocarbons. Preference is given to using toluene.

The concentration of the aluminoxane in the solution is in the range from about 1% by weight to the saturation limit, preferably from 5 to 30% by weight, in each case based on the total amount of solution. The metallocene can be used in the same concentration, but it is preferably used in an amount of $10^{-4}$–1 mol per mole of aluminoxane. The preactivation time is from 5 minutes to 60 hours, preferably from 5 to 60 minutes. The preactivation is carried out at a temperature of from $-78°$ to $100°$ C., preferably from $0°$ to $70°$ C.

The metallocene compound is here preferably used in a concentration, based on the transition metal, of from $10^{-3}$ to $10^{-8}$, preferably from $10^{-4}$ to $10^{-7}$, mol of transition metal per $dm^3$ of solvent or per $dm^3$ of reactor volume. The aluminoxane is preferably used in a concentration of from $10^{-6}$ to $10^{-1}$ mol, preferably from $10^{-5}$ to $10^{-2}$ mol, per $dm^3$ of solvent or per $dm^3$ of reactor volume. The other specified cocatalysts are used in approximately equal amounts to the metallocene compound. In principle, however, higher concentrations are also possible.

To remove catalyst poisons present in the olefin, purification using an aluminum compound, preferably an aluminum alkyl such as trimethylaluminum or triethylaluminum, is advantageous. This purification can either be carried out in the polymerization system itself or the olefin is brought into contact with the aluminum compound prior to its addition to the polymerization system and is subsequently separated off again.

As molecular weight regulator and/or for increasing the activity, hydrogen can be added in the process of the invention. This enables low molecular weight polyolefins such as waxes to be obtained.

In the process of the invention, the metallocene compound is preferably reacted with the cocatalyst outside the polymerization reactor in a separate step using a suitable solvent. It can here be applied to a support.

In the process of the invention, a prepolymerization can be carried out with the aid of the metallocene compound. The (or one of the) olefin(s) used in the polymerization is preferably used for the prepolymerization.

The catalyst used in the process of the invention can be. Supported. Application to a support allows, for example, the particle morphology of the polyolefin prepared to be controlled. The metallocene compound can here first be reacted with the support and subsequently with the cocatalyst. The cocatalyst can also first be supported and subsequently reacted with the metallocene compound. It is also possible to support the reaction product of metallocene compound and cocatalyst. Suitable support materials are, for example, silica gels, aluminum oxides, solid aluminoxane or other inorganic support materials such as, for example, magnesium chloride. Another suitable support material is a polyolefin powder in finely divided form. The preparation of the supported cocatalyst can be carried out, for example, as described in EP 567 952.

If the polymerization is carried out as a suspension or solution polymerization, an inert solvent customary for the Ziegler low-pressure process is used. For example, the polymerization is carried out in an aliphatic or cycloaliphatic hydrocarbon; examples of these which may be mentioned are propane, butane, hexane, heptane, isooctane, cyclohexane, methylcyclohexane. Furthermore, a petroleum fraction or hydrogenated diesel oil fraction can be used. It is also possible to use toluene.

If inert solvents are used, the monomers are metered in in gaseous or liquid form.

The duration of the polymerization can be as desired, since the catalyst system to be used in the process of the invention shows only a slight time-dependent fall in the polymerization activity.

The polymers prepared by the process of the invention are suitable, in particular, for producing shaped articles such as films, plates or large hollow bodies (e.g. pipes).

The metallocene compound of the invention enables the synthetic complication of introducing a bridge between the ligands to be omitted. This makes the preparation of the metallocenes cheaper and avoids losses in yield.

In addition, both the racemic and meso forms of the metallocene compound of the invention have a comparable polymerization activity and also degree of comonomer incorporation, so that the complicated separation of racemic and meso forms can be omitted, in particular if the metallocene compound is used for copolymerization.

The metallocene compound of the invention can advantageously be used for preparing copolymers, in particular ethylene-containing copolymers, having a low density, such as LLDPE. In particular, the metallocene compound of the invention is suitable for preparing copolymers, in particular ethylene-containing copolymers, having a low density using low comonomer concentrations. This is advantageous particularly when a low comonomer concentration is to be maintained for technical or economic considerations, e.g. when, in the gas-phase polymerization, comonomers condense when the saturation concentration is exceeded and thus cause technical difficulties. Particularly advantageous is the use of the metallocene compound of the invention in copolymerization using relatively high-boiling comonomers in the gas-phase polymerization.

The metallocene compound of the invention has a high degree of comonomer incorporation and is suitable for the preparation of comonomer-rich copolymers such as elastomers.

EXAMPLES

The following examples illustrate the invention:

Preparation and handling of organometallic compounds were carried out with exclusion of air and moisture under argon protective gas (Schlenk technique). All solvents required were, prior to use, purified by boiling for a number of hours over a suitable desiccant and subsequent distillation under argon.

The compounds were characterized using $^1$H-NMR, $^{13}$C-NMR and IR spectroscopy.

The polymer melting points $T_m$ given are taken from a DSC measurement for the second melting at a heating rate of $10°$ C./min.

Toluene-soluble methylaluminoxane is obtained as a 10% strength toluene solution from WITCO and, according to an aluminum determination, contains 36 mg Al/ml.

The comonomer incorporation is determined using $^{13}$C-NMR in accordance with the method of Randall (Macromolecules 1994, 27, 2120).

The density is determined by the gradient method in accordance with ISO 1183-1987.

Example 1

Bis(2-methyl-4,5-benzoindenyl)zirconium dichloride: 30 g (166 mmol) of 2-methyl-4,5-benzoindene are dissolved in 500 ml of toluene and admixed with 62 ml (166 mmol) of a 2.68 molar butyllithium solution in toluene. The suspension is stirred for a further 1 hour at 60° C. and subsequently cooled to −30° C. 29.7 g (78.9 mmol) of ZrCl$_4$.2THF are added and the reaction mixture is allowed to warm up to room temperature over 12 hours. The yellow suspension is filtered through a glass frit and washed with 200 ml of THF. The filtrate is reduced to half its volume by removing the solvent in vacuo and the solution is crystallized by storage at −30° C. The precipitate formed is filtered off and the filtrate is again reduced to half its volume. After crystallizing again, 9.1 g (22%) of meso-bis(2-methyl-4,5-benzoindenyl) zirconium dichloride containing less than 10% of the racemic compound are obtained. The residue on the glass frit is washed with 500 ml of methylene chloride and the remaining residue is dried in vacuo. This gives 7.3 g (18%) of rac-bis(2-methyl-4,5-benzoindenyl)zirconium dichloride as a lemon yellow solid.

Example 2

500 ml of diesel oil (bp. 100°–120° C.), 20 ml of hexene and 10 ml of 10% strength by weight solution of methylaluminoxane in toluene were placed in a laboratory autoclave under nitrogen and heated to 70° C. while stirring at 700 rpm. In parallel thereto, 0.1 mg of rac-bis(2-methyl-4,5-benzoindenyl)zirconium dichloride were dissolved in 1 ml of 10% strength by weight MAO solution in toluene. The polymerization is started by addition of the metallocene/MAO solution and by pressurizing with 4 bar of ethylene. After 15 minutes, the polymerization is stopped using CO$_2$ and the reactor contents are drained into 200 ml of methanolic HCl. The mixture is stirred for 5 hours to remove aluminum, the polymer is subsequently filtered off and washed with water and acetone and, to determine the yield, dried for 12 hours in vacuo at 120° C. The amount of metallocene was selected in such a way that not more than 5 g of polymer resulted. A 1 g sample is, to remove residual comonomer, dissolved in hot diesel oil (bp. 100°–120° C.), subsequently precipitated, filtered off, washed with acetone and again dried in vacuo at 120° C. The polymerization results are shown in Table 1.

Example 3

Example 2 was repeated, using 0.1 mg of meso-bis(2-methyl-4,5-benzoindenyl)zirconium dichloride as metallocene. The polymerization results are shown in Table 1.

Examples 4 and 5 (Comparative Examples)

Example 2 was repeated with 20 ml (Example 4) or 50 ml (Example 5) of hexene using the metallocene bis(methylcyclopentadienyl)zirconium dichloride. The polymerization results are shown in Table 1.

Example 6 (Comparative Example)

Example 2 was repeated with 20 ml of hexene using the metallocene ethylenebis(indenyl)zirconium dichloride. The polymerization results are shown in Table 1.

TABLE 1

| Ex. | ml hexene | mg cat. | Yield [g polymer] | T$_m$ [°C.] | Density [g/dm$^3$] | mol % hexene |
|---|---|---|---|---|---|---|
| 2 | 20 | 0.1 | 5.6 | 102.5 | 0.905 | 6.1 |
| 3 | 20 | 0.1 | 5.5 | 102.6 | 0.905 | 6 |
| C4 | 20 | 0.1 | 5.2 | 123.8 | 0.927 | 1.6 |

TABLE 1-continued

| Ex. | ml hexene | mg cat. | Yield [g polymer] | T$_m$ [°C.] | Density [g/dm$^3$] | mol % hexene |
|---|---|---|---|---|---|---|
| C5 | 50 | 0.1 | 2.1 | 122.9 | 0.911 | 1.6 |
| C6 | 20 | 0.1 | 3.8 | 106.6 | 0.909 | 5.5 |

Example 7

Supported methylaluminoxane is prepared as described in Example 13 of EP-A-567 952 (which is herewith expressly incorporated by reference) as a 13.2% strength by weight suspension in decane. The solid from 39 ml of the suspension is filtered off and admixed with 40 ml of diesel oil and 10 mg of rac-bis(2-methyl-4,5-benzoindenyl)zirconium dichloride powder, stirred for 2 hours at ambient temperature and subsequently filtered.

In parallel thereto, a 16 dm$^3$ reactor is charged with 8 dm$^3$ of iso-butane, 10 mmol of triisobutylaluminum in diesel oil and 100 ml of 1-hexene and, at 70° C, ethylene is metered in to a pressure of 30 bar.

The catalyst is metered in in butane suspension, the temperature is regulated at 70° C. and the total pressure is kept constant by metering in ethylene. At intervals of 15 minutes, a further 100 ml of hexene are metered in each time. After 1 hour, the polymerization is stopped using CO$_2$ gas. After venting and opening the reactor, 1.35 kg of LLDPE having a bulk density of 321 g/dm$^3$ and a density of 0.9105 are found. The reactor is free of deposits.

Example 8

5 mg of rac-bis(2-methyl-4,5-benzoindenyl)zirconium dichloride are dissolved in 20 ml of 10% strength methylaluminoxane solution in toluene and stirred for 0.5 hour.

In parallel thereto, a 16 dm$^3$ reactor is charged with 8 dm$^3$ of propylene and with 10 ml of 10% strength by weight triisobutylaluminum in diesel oil. After metering in the catalyst solution, polymerization is carried out for 1 hour at 70° C., stopped using CO$_2$, the reactor is vented and opened. This gives 822 g of PP having M$_n$=25100 g/mol and M$_w$/M$_n$=2.2.

We claim:

1. A metallocene compound of the formula (I)

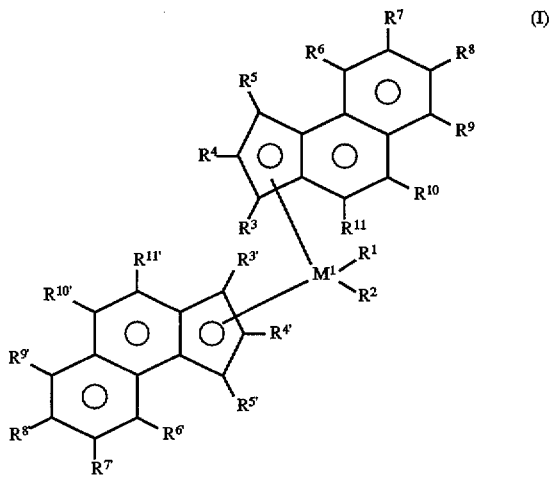

where

M$^1$ is a metal of group IVb, Vb or VIb of the Periodic Table,

R¹ and R² are identical or different and are each a hydrogen atom, a $C_1$-$C_{10}$-alkyl group, a $C_1$-$C_{10}$-alkoxy group, a $C_6$-$C_{10}$-aryl group, a $C_6$-$C_{10}$-aryloxy group, a $C_2$-$C_{10}$-alkenyl group, a $C_7$-$C_{40}$-arylalkyl group, a $C_8$-$C_{40}$-arylalkenyl group, an OH group or a halogen atom, the radicals $R^3$, $R^4$, $R^5$, $R^6$, $R^7$, $R^8$, $R^9$, $R^{10}$ and $R^{11}$ are identical or different and are each a hydrogen atom, a halogen atom, a $C_1$-$C_{20}$-hydrocarbon radical which may be halogenated, an —$NR_2$, —SR, —OR, —$OSiR_3$, —$SiR_3$ or $PR_2$ radical, where R is a halogen atom, a $C_1$-$C_{10}$-alkyl group or a $C_6$-$C_{10}$-aryl group, or two or more of the radicals $R^3$, $R^4$, $R^5$, $R^6$, $R^7$, $R^8$, $R^9$, $R^{10}$ and $R^{11}$ together with the atoms connecting them form a ring system, and the radicals $R^{3'}$, $R^{4'}$, $R^{5'}$, $R^{6'}$, $R^{7'}$, $R^{8'}$, $R^{9'}$, $R^{10'}$ and $R^{11'}$ are identical or different and are each a hydrogen atom, a halogen atom, a $C_1$-$C_{20}$-hydrocarbon radical which may be halogenated, an —$NR_2$, —SR, —OR, —$OSiR_3$, —$SiR_3$ or $PR_2$ radical, where R is a halogen atom, a $C_1$-$C_{10}$-alkyl group or a $C_6$-$C_{10}$-aryl group, or two or more of the radicals $R^{3'}$, $R^{4'}$, $R^{5'}$, $R^{6'}$, $R^{7'}$, $R^{8'}$, $R^{9'}$, $R^{10'}$ and $R^{11'}$ together with the atoms connecting them form a ring system.

2. The metallocene as claimed in claim 1, wherein the metallocene is selected from the group consisting of bis(2-methyl-4,5-benzoindenyl)zirconium dichloride, bis(4,5-benzoindenyl)zirconium dichloride, bis(2-methyl-α-acenaphthylindenyl)zirconium dichloride, bis(2-ethyl-α-acenaphthylindenyl)zirconium dichloride, bis(α-acenaphthylindenyl)zirconium dichloride, (2-methyl-4,5-benzoindenyl)(4,5-benzoindenyl)zirconium dichloride, (2-methyl-4,5-benzoindenyl)(2-methyl-α-acenaphthylindenyl)zirconium dichloride, bis(2-methyl-4,5-benzoindenyl)titanium dichloride, bis(2-methyl-4,5-benzoindenyl)hafnium dichloride, bis(2-methyl-4,5-benzoindenyl)dimethylzirconium, and bis(4,5-benzoindenyl)dimethylzirconium.

3. The metallocene as claimed in claim 1, wherein $M^1$ is a metal of group IVb and $R^1$ and $R^2$ are identical.

4. The metallocene as claimed in claim 3, wherein $M^1$ is Zr, Hf or Ti and $R^1$ and $R^2$ are identical and are $C_1$-$C_{10}$-alkyl group, $C_7$-$C_{15}$-arylalkyl group, F, Cl, Br or I.

5. The metallocene as claimed in claim 4, wherein $M^1$ is Zr and $R^1$ and $R^2$ are Cl.

6. The metallocene as claimed in claim 1, wherein $R^3$, $R^4$, $R^5$, $R^6$, $R^7$, $R^8$, $R^9$, $R^{10}$ and $R^{11}$ are identical or different and are a hydrogen atom, $C_1$-$C_{20}$-hydrocarbon radical or two or more of the radicals $R^3$, $R^4$, $R^5$, $R^6$, $R^7$, $R^8$, $R^9$, $R^{10}$ and $R^{11}$ together with the atoms connecting them form a ring system.

7. The metallocene as claimed in claim 5, wherein $R^3$, $R^4$, $R^5$, $R^6$, $R^7$, $R^8$, $R^9$, $R^{10}$ and $R^{11}$ are identical or different and are a hydrogen atom, $C_1$-$C_{20}$-alkyl group, $C_6$-$C_{14}$-aryl group, $C_2$-$C_{20}$-alkenyl group, $C_7$-$C_{40}$-arylalkyl group or $C_8$-$C_{40}$-arylalkenyl group, or two or more of the radicals $R^3$, $R^4$, $R^5$, $R^6$, $R^7$, $R^8$, $R^9$, $R^{10}$ and $R^{11}$ together with the atoms connecting them form a ring system.

8. The metallocene as claimed in claim 1, wherein $R^{3'}$, $R^{4'}$, $R^{5'}$, $R^{6'}$, $R^{7'}$, $R^{8'}$, $R^{9'}$, $R^{10'}$ and $R^{11'}$ are identical or different and are a hydrogen atom, $C_1$-$C_{20}$-hydrocarbon radical or two or more of the radicals $R^{3'}$, $R^{4'}$, $R^{5'}$, $R^{6'}$, $R^{7'}$, $R^{8'}$, $R^{9'}$, $R^{10'}$ and $R^{11'}$ together with the atoms connecting them form a ring system.

9. The metallocene as claimed in claim 7, wherein $R^{3'}$, $R^{4'}$, $R^{5'}$, $R^{6'}$, $R^{7'}$, $R^{8'}$, $R^{9'}$, $R^{10'}$ and $R^{11'}$ are identical or different and are a hydrogen atom, $C_1$-$C_{20}$-alkyl group, $C_6$-$C_{14}$-aryl group, $C_2$-$C_{20}$-alkenyl group, $C_7$-$C_{40}$-arylalkyl group or $C_8$-$C_{40}$-arylalkenyl group, or two or more of the radicals $R^{3'}$, $R^{4'}$, $R^{5'}$, $R^{6'}$, $R^{7'}$, $R^{8'}$, $R^{9'}$, $R^{10'}$ and $R^{11'}$ together with the atoms connecting them form a ring system.

10. A catalyst comprising at least one metallocene compound as claimed in claim 1 and a cocatalyst.

11. A catalyst as claimed in claim 10, wherein the cocatalyst is an aluminoxane.

12. A catalyst as claimed in claim 10, wherein the catalyst is supported and/or prepolymerized.

13. A catalyst comprising at least one metallocene compound as claimed in claim 2, and a cocatalyst that is an aluminumoxane of the formula IIa

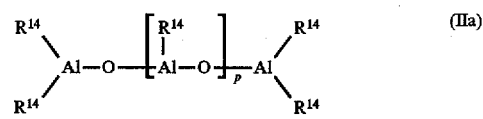

for the linear type and/or of the formula IIb

for the cyclic type where, in the formulae IIa and IIb, the radicals $R^{14}$ are identical or different and are each hydrogen or a $C_1$-$C_{20}$-hydrocarbon group and p is an integer from 2 to 50.

14. The catalyst as claimed in claim 13, wherein p is from 10 to 35 and the radical $R^{14}$ are identical and are hydrogen, methyl, isopropyl, phenyl or benzyl.

15. The catalyst as claimed in claim 14, wherein the radicals of $R^{14}$ are methyl.

16. The catalyst as claimed in claim 15, wherein the catalyst is supported and/or prepolymerized.

17. A process for preparing an olefin polymer comprising polymerizing at least one olefin in the presence of the catalyst as claimed in claim 10.

18. A process for preparing an olefin polymer comprising polymerizing at least one olefin in the presence of the catalyst as claimed in claim 15.

19. An olefin polymer prepared by the process as claimed in claim 17.

* * * * *